(12) United States Patent
Skarping et al.

(10) Patent No.: US 7,700,045 B2
(45) Date of Patent: Apr. 20, 2010

(54) SAMPLING DEVICE

(75) Inventors: Gunnar Skarping, Hässleholm (SE); Marianne Dalene, Hässleholm (SE)

(73) Assignee: Provtagaren AB, Hassleholm (SE)

( * ) Notice: Subject to any disclaimer, the term of this patent is extended or adjusted under 35 U.S.C. 154(b) by 1092 days.

(21) Appl. No.: 11/361,689

(22) Filed: Feb. 24, 2006

(65) Prior Publication Data

US 2006/0239857 A1    Oct. 26, 2006

Related U.S. Application Data

(63) Continuation-in-part of application No. 09/980,346, filed as application No. PCT/SE00/01152 on Jun. 2, 2000, now abandoned.

(60) Provisional application No. 60/138,053, filed on Jun. 8, 1999.

(30) Foreign Application Priority Data

Jun. 3, 1999    (SE) .................................... 9902089

(51) Int. Cl.
*B01L 3/00*    (2006.01)
(52) U.S. Cl. ............................. 422/99; 422/57; 422/58; 422/83; 422/88; 422/312; 436/109; 436/111; 436/808
(58) Field of Classification Search .................. 422/99; 436/53, 109
See application file for complete search history.

(56) References Cited

U.S. PATENT DOCUMENTS 3,533,750 A    10/1970    Belisle
4,381,408 A    4/1983    Rounbehler et al.

(Continued)

FOREIGN PATENT DOCUMENTS

SU    1724305    4/1992

(Continued)

OTHER PUBLICATIONS

SU 1724305 A1 (As UKR Surface Chem Inst) Apr. 7, 1992 (abstract) World Patents Index (online). London, U.K.: Derwent Publications, Ltd. (retrieved on Apr. 4, 2000). Retrieved from: EPO WPI Database. DW 199311, Accession No. 1993-091795.

(Continued)

*Primary Examiner*—Robert J Hill, Jr.
*Assistant Examiner*—Dwan A Gerido
(74) *Attorney, Agent, or Firm*—Weingarten, Schurgin, Gagnebin & Lebovici LLP

(57) ABSTRACT

A sampling device is described for analysis of a substance, wherein the substance is selected from the group consisting of isocyanates, aminoisocyanates, isothiocyanates, anhydrides, amines and carboxylic acids and can be present in both gas and particle phases in an air flow passed, for sampling, through the sampling device, said device comprising:
  a) an adsorption device comprising a coating, wherein said coating comprises a reagent mixture in the form of one or more primary or secondary amines and an acidic compound having the ability to form a salt (or ionic bond) with the amine(s) for adsorption of and reaction with the substance in the gas phase of the air flow; and
  b) a filter device comprising said mixture of amine(s) and acidic compound for adsorption of and reaction with the substance in the particle phase of the air flow.

29 Claims, 2 Drawing Sheets

U.S. PATENT DOCUMENTS

| | | | |
|---|---|---|---|
| 5,242,836 | A | 9/1993 | Ruse |
| 5,302,191 | A | 4/1994 | Koutrakis et al. |
| 5,763,096 | A | 6/1998 | Takahashi et al. |
| 6,226,852 | B1 | 5/2001 | Gundel et al. |
| 6,475,802 | B2 | 11/2002 | Schaedlich et al. |

FOREIGN PATENT DOCUMENTS

| | | | |
|---|---|---|---|
| WO | WO/00/75622 | * | 12/2000 |

OTHER PUBLICATIONS

Journal of Environmental Monitoring, 2005, 7(5), 469-474. "A Chemisoorptive cylindrical denuder designed for personal exposure measurements . . . diisocyanate." Nordqvist et al.

"Aerosol/Vapor Partitioning of Monmeric Isocyanates," pp. 1-12, Poovey et al. Tulane University School of Public Health and Tropical Medicine. No Date. Obtained from Google Search.

Anal Bioanal Chem. Mar. 2003; 375(6)L:786-91. Epub Mar. 11, 2003. "Evaluation of denuder sampling for a mixture of three common gaseous diisocyanates." Dept. of Analytic Chemistry, Stockholm University.

"Development and Evaluation of a Denuder-filter System Designed for Sampling Diisocyanate Aerosols", PhD Dissertation by Yvonne Nordqvist, Stockholm University, Dept of Analytic Chemistry, 2004.

Fresenius J Anal Chem. Sep. 2001; 371 (1 ):39-43, "Comparison of denuder and impinger sampling for determination of gaseous toluene diisocyanate" by Nordqvist et al.

Marand, Åsa, et al.: "Solvent-free sampling with di-n-buylamine for monitoring of isocyanates in air," Stockholm University 2004 (Paper IV, p. 4-5).

* cited by examiner

FIG. 1
FIG. 2
FIG. 3
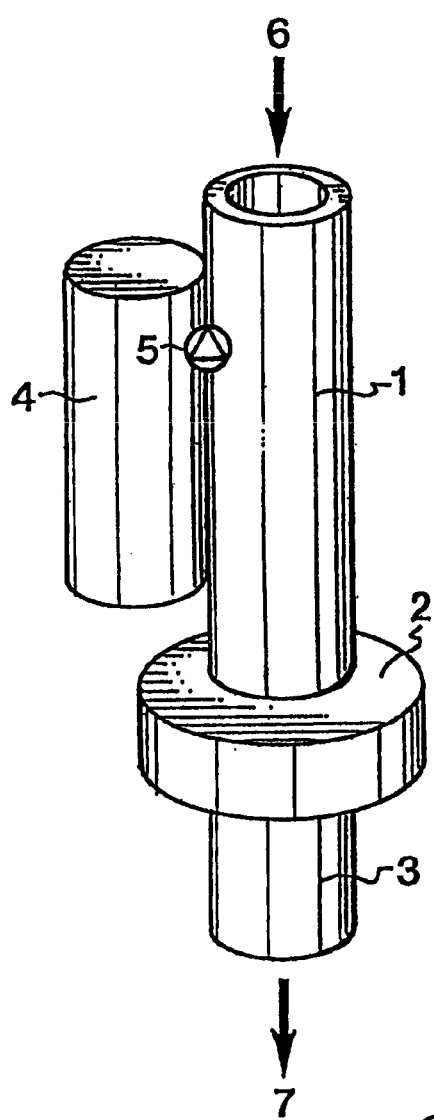
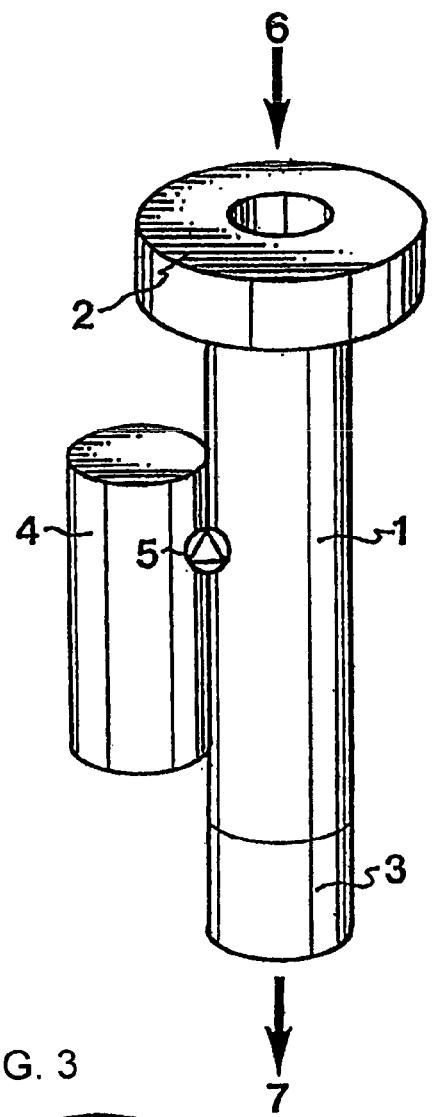
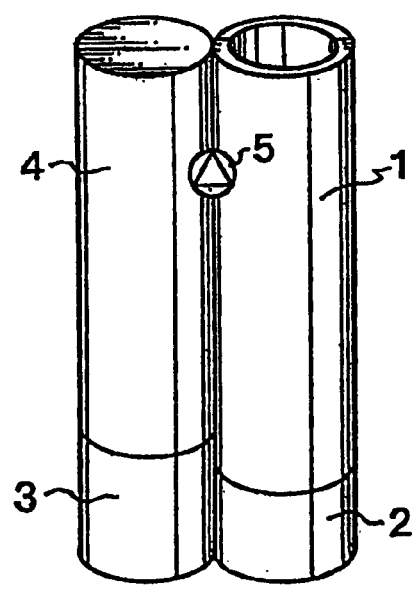

SAMPLING DEVICE

This application is a continuation-in-part of U.S. patent application Ser. No. 09/980,346 filed Jan. 23, 2002 now abandoned, entitled SAMPLING DEVICE; which was a §371 national stage of International Application PCT/SE00/01152 filed Jun. 2, 2000; which claims benefit of U.S. No. 60/138,053 filed Jun. 8, 1999, and Swedish application No. 9902089-3 filed Jun. 3, 1999.

FIELD OF THE INVENTION

The present invention relates to a device and a method of sampling for analysis of isocyanates, aminoisocyanates, anhydrides, amines, isothiocyanates and carboxylic acids which are present in both gas and particle phase in an air flow.

BACKGROUND OF THE INVENTION

Polyurethane (PUR) products frequently occur in industry, in particular in manufacturing and handling polyurethane foam, elastomers, adhesives and lacquers. Polyurethane is produced by the reaction of a bifunctional isocyanate with a polyfunctional alcohol. The satisfactory technical qualities of polyurethane have resulted in a large increase of its use and application fields during the last decade. In connection with thermal decomposition of polyurethanes, however, the formation of isocyanates, aminoisocyanates and amines might occur, and extremely high contents can be found in air, e.g. when welding automobile sheet steel. Besides the known types of isocyanate, also new types of aliphatic isocyanates have been detected, in connection with e.g. heat treatment of car paint. Most of the isocyanates formed have been found to be represented by so-called low-molecular isocyanates. During short periods of time (peak exposure) particularly high isocyanate contents can be present, as is the case, for instance, when welding. Of all the dangerous substances on the limit value list, isocyanates have the lowest permissible contents. Exposure to this new type of isocyanates was previously unheard of. Isocyanates in both gas and particle phase have been detected in connection with welding, grinding and cutting of painted automobile sheet steel, and respirable particles in high contents containing isocyanates have been detected. In thermal decomposition products of painted automobile sheet steel, detection has been made of, among other things, methyl isocyanate (MIC), ethyl isocyanate (EIC), propyl isocyanate (PIC), phenyl isocyanate (PhI), 1,6-hexamethylene diisocyanate (HDI), isophorone diisocyanate (IPDI), 2,4- and 2,6-diisocyanate toluene (TDI) and 4,4-methylene diphenyl-diisocyanate (MDI).

In thermal decomposition of phenol/formaldehyde/urea-(FFU)-plastic, isocyanic acid and methyl isocyanate are formed. FFU plastic is used, among other things, in wood glue and as a binder in mineral wool (and bakelite), which is frequently used as insulation for ovens and furnaces in industrial and domestic use. New fields of application in which exposure to isocyanates has been detected are the soldering and processing of printed circuit boards in the electronic industry, the welding, grinding and cutting of painted sheet steel in the automobile industry and the welding of lacquered copper pipes. Isocyanates have a varying degree of toxicity to the organism depending on their chemical and physical form. As a result, the hygienic limit values have been set at an extremely low level in all countries. For the exposed individual, the degree of exposure to isocyanates varies considerably in different operations during a working day and in connection with breakdowns. Thermal decomposition products from PUR constitute a special problem, since new and completely unknown isocyanates are formed, whose toxicity has not yet been analyzed in a satisfactory manner. Furthermore, the increasingly sophisticated measuring methods have revealed exposure to isocyanates in an increasing number of operations in industry.

To sum up, there is a number of operations in numerous working areas where people are daily exposed to or at risk being exposed to isocyanates at a varying degree. Considering the ominous tendency of isocyanates to cause respiratory diseases and the fact that there are some carcinogenic substances among the thermal decomposition products of polyurethane, e.g. 2,4-diamine toluene (TDA), 4,4-methylene diamine (MDA) and MOCA, it is very important to measure in a reliable, sensitive and rapid manner any presence of isocyanates, but also other decomposition products dangerous to health, in environments where there is such a risk.

Due to the high degree of reactivity of the isocyanates with other substances containing active hydrogen, the major part of the methods utilized for measuring in air flows are based on derivatisation in connection with the sampling step in order to protect the isocyanate group and allowing a selective determination of the isocyanates. A number of reagents and methods have been presented for the determination of isocyanates. However, there is only a limited amount of information about the reaction rate of isocyanates, and losses due to the presence of interfering substances has been reported, for instance, for 1-(2-methoxyphenyl)piperazine (2 MP) and MAMA as derivatisation reagents for 2,4- and 2,6-TDI. A method recently developed by the present inventor has a number of advantages in comparison with the above-mentioned MAMA method. This new method, which is called the DBA method due to the use of di-n-butylamine as reagent, allows the analysis of several new types of isocyanates and has been suggested as an international ISO reference method. The DBA method is based on the gathering of isocyanates in impinger bottles containing DBA in toluene and having a filter which is coupled in series and situated after the impinger bottle in the flow direction. In a sampling process, DBA solution and toluene are added to an impinger bottle. Subsequently, the sample flow is calibrated. An air flow is drawn through a tube immersed in the reagent solution, and isocyanates in the air flow react with DBA in the solution. Non-reacted gaseous isocyanates which have passed the solution are drawn through a filter which is provided with a reagent and arranged in connection with the suction device. Thus on this filter isocyanates which have not reacted with the reagent solution are bound. After completed sampling, the DBA solution with bound isocyanates is conveyed to and the filter is applied to one and the same test tube for further transport to an analysis step. Impinger bottles containing 10 ml 0.01 mole DBA in toluene have been used. Deuterium-labeled isocyanate DBA derivates are added to the samples and used as internal standards. Carbamate esters are formed by adding 2 ml 5 M NaOH, 10 µl pyridine and 50 µl ethyl chloroformate to the samples. The so-called DBA method has been tested for isocyanates in connection with spray painting with two typical biuret and isocyanurate adducts, HDI, IPD, polymeric MDI, TDI and thermal decomposition products from PUR plastic. High reaction rates for the reaction of the isocyanates with DBA have been observed, and the method is not sensitive to interfering substances. Since DBA is easy to eliminate in connection with the processing of the sample, the subsequent chromatographic determination is facilitated, which allows the use of the reagent in high contents. Before the chromatographic determination, the organic phase is separated and evaporated until it is dry. The rest is dissolved in 500

µl acetonitrile, after which the solution is injected into a liquid chromatographic (LC-mass-spectrometric (MS)) system.

Other methods used for the determination of isocyanates have a number of drawbacks. Among other things, isocyanates which are present in both gas phase and particle phase in the air flow cannot be bound to the reagent in a satisfactory manner. Isocyanates which are present on and/or in particles, such as dust, will not be completely accessible to analysis, but will be polymerized to a kind of lump. Moreover, the reaction of the reagent with isocyanates is slow and negatively affected by interference from other substances present. In addition, the minimal sampling volume is about 0.5 l air, whereas the air flow which is obtained by means of a battery-operated air pump usually amounts to about 1 l/min. Furthermore, conventional sampling devices require manual adding of solvents and reagents as well as manual dismounting to convey the reagent liquid and the filter with bound isocyanates to the final analysis test tube. Another drawback is that such a sampling device can be tampered with to obtain false results.

In view of this, there is a great demand for an improved device and an improved method for sampling isocyanates, but also other products dangerous to health, such as aminoisocyanates, amines, isothiocyanates, anhydrides and carboxylic acids, in a rapid, reliable, precise and tamperproof manner.

SUMMARY OF THE INVENTION

An object of the present invention is to eliminate the above-mentioned problems and provide a device and a method for improved sampling in an air flow for the analysis of isocyanates, aminoisocyanates, anhydrides, amines, isothiocyanates and carboxylic acids which are present in both gas and particle phase.

According to the invention, this object is achieved by means of a device and a method, respectively, of the type mentioned by way of introduction, which have the features stated in the appended claims 1 and 21, respectively. Preferred embodiments of the sampling device and the method, respectively, are defined in the dependent claims.

According to one aspect, the present invention relates to a sampling device for the analysis of substances which are present in both gas and particle phase in an air flow.

According to another aspect, the invention relates to a method for sampling in an air flow by means of the sampling device according to the present invention.

According to a further aspect, the present invention relates to a kit containing a set of a plurality of sampling devices which contain different reagents for taking samples from different substances in an air flow, which is specified in claim 17.

According to yet another aspect, the present invention relates to a method for binding a reagent to a surface, preferably to a surface in an adsorption device 1 and a filter device 2 in the sampling device according to the present invention, which is specified in claim 18.

BRIEF DESCRIPTION OF THE DRAWINGS

FIG. 1 schematically shows one embodiment of a sampling device according to the present invention.

FIG. 2 schematically shows an alternative embodiment of the sampling device according to the present invention.

FIG. 3 schematically shows a further alternative embodiment of the sampling device according to the present invention.

DESCRIPTION OF PREFERRED EMBODIMENTS

Figure 4:
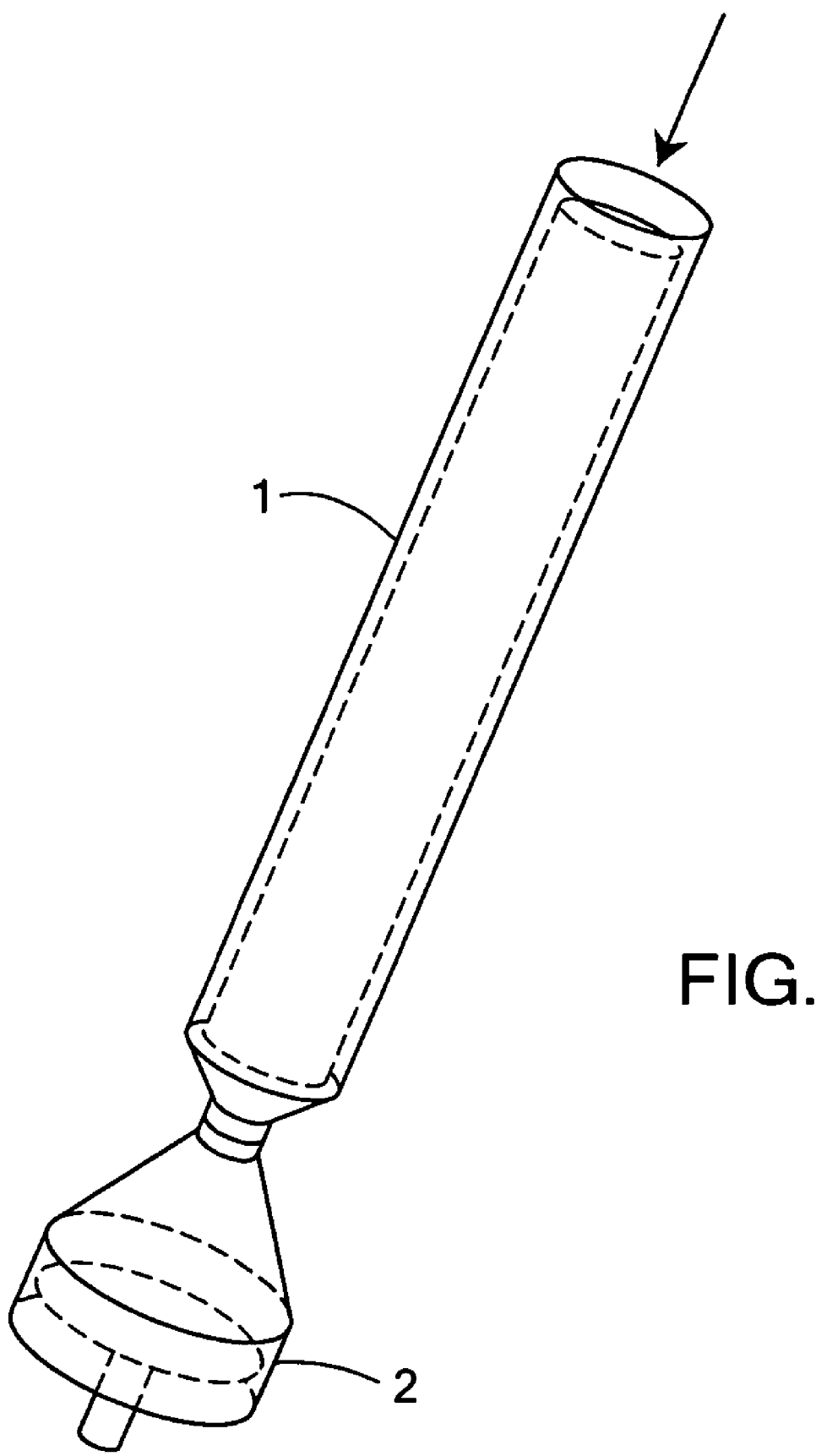
FIG. 4 schematically shows a detailed embodiment of the sampling device according to the present invention.

The present invention is, among other things, based on a new method for the immobilization of reagents in the form of volatile primary and secondary amines on a surface. Since a number of such usable reagents are volatile, there is a great demand for being able to immobilize or stabilize reagents on surfaces, for instance in adsorption devices of different kind, in such a manner that the volatility of the reagent is reduced at the same time as its reactivity is maintained. This problem has been solved by the present inventor by first mixing the reagent with a carboxylic acid or other acidic compound. In the preferred embodiment, the carboxylic function of the mixture then provides stability to the reagent. There is an excess of primary or secondary amine in relation to the carboxylic acid. Subsequently, the mixture is contacted with the surface on which the reagent is intended to be immobilized or applied, e.g. on the inside of tubes or on particles or spheres of different kind and/or on a strip inserted in a tube. Due to the surface tension, the mixture is partially adsorbed physically on the surface as a coating, and the otherwise volatile reagent is retained and can pursue its activity. The immobilization procedure is disclosed in detail by Marand, Åsa; Karlsson, Daniel; Dalene, Marianne; and Skarping, Gunnar, in "Isocyanates and Amines—sampling and Analytical procedures," Stockholm University 2004 (Solvent-free sampling with di-n-butylamine for monitoring of isocyanates in air), (Paper IV, p. 4-5). Any carboxylic acids can be used to contribute to the carboxylic acid function, e.g. both monovalent and polyvalent, saturated and unsaturated, but in a preferred embodiment use is made of formic acid (HCOOH), acetic acid ($CH_3COOH$) or propionic acid ($C_2H_5COOH$). Combinations of one or more different carboxylic acids are also usable Further, any acidic compound having the ability to form a salt (or ionic bond) with the amine(s) can be used instead of the carboxylic acid in the immobilization reaction, e.g., HCl, $H_2CO_3$, etc.

The primary or secondary amine which constitutes the reagent can be any amine which in free form is volatile and which has a molecular weight inferior to 300. Di-n-butylamine (DBA) is particularly preferred when analyzing isocyanates and aminoisocyanates. Other examples of usable amines are other dialkylamines which meet the above restriction on molecular weight, e.g. dimethylamine, di-isobutylamine, dipropylamine, di-isoproylamine, di-isobutylamine, etc.

In one embodiment the adsorption device 1 is intentionally impregnated with a larger amount of DBA as compared to the filter device 2, with the aim of continuously refreshing the filter device 2 with DBA. The release of DBA from the adsorption device 1 may be demonstrated by sampling in a test chamber using a blank filter device 2, i.e. without any impregnated DBA. Isocyanate-DBA derivatives obtained is then found on the blank filter device 2 in similar extent as on an impregnated device 2 filter. The combination of using both an impregnated filter device 2 and continuous refreshing of the reagent on the filter device 2 makes the sampling device more resistant towards interferences.

The expression "primary or secondary amine" which is used here also comprises an amine which, in addition to the amine group, can contain one or more other functional groups which can facilitate the immobilization and/or adsorption of and reaction with the sample substance. As examples of such amines, mention can be made of alkanolamines, e.g. ethanolamines.

The substances, from which samples are to be taken by means of the method and the sampling device according to the present invention, are primarily isocyanates, aminoisocyanates and amines, but also isothiocyanates and carboxylic acids are possible. As mentioned above, these substances are frequently present in both gas and particle phase, which has previously made it more difficult to carry out a reliable analysis. Moreover, many of these compounds are volatile and so reactive that samples cannot be taken without chemical change thereof.

The sampling device according to the present invention comprises an adsorption device 1 which, in one embodiment shown in FIG. 1, is substantially elongated, preferably tubular or hollow and cylindrical, the proportion of the length to the inner diameter being more than 5, preferably about 10. Such an adsorption tube, which is also called a "denuder", can have a length of 1 cm to 1 m and an inner diameter of 0.1 mm to 1 cm. The adsorption device 1 can be made of plastic or any other low-weight material. In the preferred embodiment with a tubular adsorption device 1, the reagent is applied or immobilized on the inner walls of the tube and mixed with carboxylic acid.

When using the sampling device, sample air containing the substance which is to be analyzed is allowed to pass through the adsorption device 1, the major content of the substance in gas phase first being adsorbed on and subsequently reacting with the reagent which is immobilized on the inside of the tube walls. However, the portion of the substance which is bound on and/or in particles is passed through the adsorption device 1 together with a small portion of the substance in gas phase which has not been adsorbed. In another embodiment the reagent is also or instead immobized on the surface of a strip inserted in the adsorption device 1.

In still another embodiment, the adsorption device 1 can consist of a bed or a plate of packed particles, e.g. of glass, silicon dioxide or plastic, on which the reagent has been immobilized in the above described manner. The dimensions of the bed are not critical, but it is preferably formed as a flat cylinder.

The sampling device according to the present invention also comprises a filter device 2, which is not critical as to dimensions, but is preferably formed as a substantially flat cylinder having an inner diameter which is greater than or equal to that of the adsorption device 1. The filter device can be of any type which provides a separation of the particle phase and the gas phase in the flow and is, for instance, made of a glass or plastic material having a pore diameter of about 0.1-20 μm, preferably 0.3-0.5 μm, and most preferably about 0.4 μm. The filter device 2 is impregnated with immobilized reagent in the same way as the adsorption device 1. Substances in solid phase, i.e. that are present on or in particles, in the passing air flow are dissolved from the particles in the filter device 2 and react in the same way with immobilized reagent. In the case of DBA as reagent for the reaction with and binding of isocyanates, aminoisocyanates, anhydrides, and amines, the binding reaction takes place immediately and is not affected by interfering substances in the sample.

The sampling device according to the present invention further comprises a pumping or suction device 3 which can be of any type providing the required passage of the air flow through the sampling device, but it is preferably a suction device in the form of a vacuum tube or a displacement pump, such as a hose pump, diaphragm pump, injection pump or a gear-type pump. In one embodiment, this device is preferably arranged in the lower end of the sampling device, that is after the end of the filter device 2 for the discharge of the air flow. In addition, the pump or suction device 3 should not be integrated in the sampling device, but be usable more than once in contrast to a disposable sampling device. Furthermore, it should be provided with a measuring device for determining the desired amount of air that is to pass. This amount is controlled by the permissible value limit for the substance involved. The pump or suction device 3 can also be adjusted so that the passage of air is controlled in such a manner that a constant air flow is obtained during the time of sampling.

As shown in FIG. 1, in one embodiment of the sampling device according to the present invention the adsorption device 1, the filter device 2 and the pump or suction device 3 are arranged in such a manner that the filter device 2 is arranged between the adsorption device 1 and the pump or suction device 3. Moreover, in this preferred embodiment the adsorption device 1 is a cylindrical adsorbent tube (denuder) comprising a reagent which has been immobilized or applied on the inside of the tube. In operation, air enters through an air inlet 6, through the adsorbent tube 1 and then through the filter device 2 before the air flow leaves through an air outlet 7 in connection with the lower end of the filter device 2. In one preferred embodiment, an air flow containing isocyanates, aminoisocyanates, anhydrides, isothiocyanates, amines and/or carboxylic acids passes through the sampling device, whose adsorbent tube 1 and filter device 2 are impregnated with di-n-butylamine (DBA). The major content of these substances in gas phase are adsorbed in and react with the reagent in the adsorption tube 1, whereas the major content of these substances in particle phase are adsorbed in and react with the reagent in the filter device 2.

However, as regards amines in the air flow, no reaction takes place with the reagent, but the amines form ion pairs with the carboxylic acids in the coating consisting of the mixture of reagent and carboxylic acids, which results in the formation of a salt.

In FIG. 1 a reagent container 4 connected to the adsorption device via a switch device 5 is shown. However, in a more preferred embodiment the sampling device 1 lacks said reagent container 4 and switch device 5.

FIG. 2 shows an alternative embodiment of the sampling device according to the present invention. The only difference in relation to the sampling device in FIG. 1 is that the adsorption device 1 and the filter device 2 are inverted, which means that as an air flow passes the major content of the substance in particle phase is first adsorbed, after which the major content of the substances in gas phase is adsorbed.

In addition, as stated above, the sampling device according to the present invention may comprise a reagent container 4. When present, the reagent container 4 contains the same reagent as that immobilized in mixture with carboxylic acid in the adsorbent device 1 and the filter device 2. However, there is no carboxylic acid in the reagent container 4, and the reagent can be more or less dissolved in an organic solvent, e.g. toluene or acetonitrile, but not in alcohol. The design of the reagent container 4 is not critical, but it is preferably tubular and arranged in parallel with the adsorption tube 1. Alternatively, the reagent container 4 can be arranged concentrically with the adsorption tube 1 and thus enclose the same. Moreover, the reagent container 4 can alternatively be connected to the filter device 2. In one embodiment, the reagent container 4 is, however, connected to the tubular adsorbent device 1. When a desired air flow has passed through the sampling device according to the present invention, the air inlet 6 and the air outlet 7 are closed by means of suitable conventional closing devices. Thus a closed system is provided, in which, however, there is usually a small amount of non-adsorbed substance left in both gas phase and particle phase. To allow a complete and exact analysis of the substance which is to be analyzed, e.g. isocyanates, the reagent is let into this closed system from the reagent container 4 and reacts with the above non-reacted substance. Preferably, this takes place essentially automatically when the sampling device has been closed, but can also be carried out manually with the aid of a control means which is arranged on the outside of the sampling device. The conveyance of the reagent can, for instance, take place automatically the moment the sampling device, after sampling, is removed from its position, e.g. some kind of attachment. There is, of course, an excess of reagent in the reagent container 4 in relation to the estimated amount of non-reacted substance in the above-mentioned closed system.

The reagent container 4 can be integrated in the sampling device or detachably arranged. The switch device 5, which is situated between the reagent container 4 and the adsorption device 1 or the filter device 2, can be any conventional valve which can be opened and closed and which secures the conveyance of reagent to the adsorption device 1 and the filter device 2.

In the more preferred embodiment, when the sampling device 1 lacks the reagent container 4 and the switch device 5, the sampling device 1 may be directly analysed without any further wet chemical steps when the desired air flow has passed and the air inset 6 and the air outlet 7 have been closed.

As mentioned above, the part of the sampling device which includes the adsorption device 1 and the filter device 2 can be made in one piece. Thus a spill-proof and tamperproof sampling device that is easy to handle is provided for exact measuring of the amount of a particular substance in an air flow. In addition, the sampling device can easily be kept in one's pocket, and in a manner which is advantageous in terms of security it can easily be sent on for a final analysis, e.g. by means of liquid chromatography and mass spectrometry.

If, before sampling, the sampling device is to be stored for such a long time that the stability of the reagent immobilized in the adsorption device 1 and the filter device 2 is at risk, the immobilization can instead take place immediately before the sampling by adding the mixture of reagent and carboxylic acid to the devices 1 and 2, but this must be done early enough to allow a complete coating and immobilization to take place. This so-called activation of the sampling device can be included as an optional step in the sampling method, in particular when using unstable reagents, e.g. for measuring aldehydes. Before the activation step, the mixture can be stored in a special container which is connected to the sampling device, and the addition can be carried out by means of a switch device, e.g. a valve, which can be controlled manually or more or less automatically. However, the reagent immobilized in the adsorption device 1 is stable during several years.

In the sampling method according to the present device, the inventive sampling device, which has been manufactured according to the above-described method for immobilization of the reagent, is placed or kept at the location where the sampling of the air flow is to take place for analysis of the specific substance. The pump or suction device 3 is set at a desired flow rate according to the permissible limit value for the substance to be analyzed.

By means of the present invention, the total amount of the substance in question in the air flow can thus be quantitatively determined in a manner which was previously not possible. If desired, the amount of the substance in gas phase can be determined separately, as well as the amount of the substance in the particle phase. However, in most cases it is above all interesting to determine at the same time the total amount of the substance in both gas and particle phase, which is achieved with the aid of the preferred embodiment of the present invention.

The sampling device according to the present invention can also be used for direct determination of the substance in question, in which case a color indicator, for instance, is brought into contact with the substance in or adjacent to the sampling device.

EXAMPLES

Example 1

In an experiment with one embodiment of the sampling device according to the present invention, an adsorption device (1) was used which was based on a denuder tube, whereas the filter device (2) consisted of a glass fiber filter of the type A/E (SKC, PA, USA) having a diameter of 13 mm, a thickness of 1 mm and a pore size of 0.3 µm. The denuder tube and the filter had previously been impregnated with 100 and 50 µl, respectively, of a reagent solution, which was prepared by adding 0.5 ml pure di-n-butylamine (DBA) and 0.5 ml concentrated acetic acid to 5 ml toluene under stirring. After the addition of this reagent solution to the denuder tube and the filter, respectively, the solvent was allowed to evaporate. The filter in the sampling device is placed in a filter holder made of teflon (Millipore Swinnex 13, Milford, Mass., USA).

A reagent container containing pure DBA in toluene was connected to the denuder tube in the sampling device by means of a conventional valve. In one experiment, known amounts of isocyanates, i.e. 0.3 µg phenylisocyanate, 0.3 µg hexamethylene diisocyanate and 0.4 µg toluene diisocyanate, were placed in glass tubes in front of the inlet of the sampling device. Air was passed through the sampling device by means of a conventional diaphragm pump having a flow rate of about 0.2 l/min. After 2 min, the sampling device was heated by means of a heat gun, and after a total time of sampling of 4 min the experiment was completed. DBA and toluene in the reagent container were passed through the valve into the denuder tube to react with non-reacted isocyanates in the denuder tube and the filter. The toluene which was added to the denuder tube and the filter dissolves the reaction product which is formed when the isocyanates have reacted with DBA, and therefore this reaction product is completely dissolved in the sampling device, i.e. it is not left immobilized on the inner walls of the denuder tube or on the surface of the filter. Subsequently, a predetermined amount of an internal standard in the form of deuterium-labeled isocyanates is added to the sampling device, whose inlet and outlet are then closed before transporting the sampling device to a laboratory for analysis.

Before the laboratory analysis, the sampling device was opened, and the DBA solution which was present in the same and contained the above-mentioned reaction product was conveyed to another test tube. Subsequently, the toluene was eliminated by evaporation, after which 0.5 ml acetonitrile was added. After this, the samples were ready for analysis by liquid chromatography (LC) in connection with mass spectrometry (MS). The separation of the different isocyanate reaction products was carried out by means of LC technique and MS detection. The mass spectrometer was connected in series to an LC system. Use was made of a column of Hypersil $C_{18}$ type.

The isocyanates were detected by monitoring $[M+1]^+$ ions for the DBA derivatives. Calibration plots were obtained from the proportions of the surfaces for the internal standard to those of the samples, and from which plots the amount of isocyanate in the sample was determined. The detection limits are about 0.2 µg per isocyanate and sample.

In the performed experiment, it was found that the isocyanates gathered in the sampling device at a yield of 100±10%.

Example 2

A sampling device as shown in detail in FIG. 4 consisted of a polypropylene tube (length=7 cm, inner diameter=0.8 cm) coupled in series with a 13 mm polypropylene filter holder (Swinnex 13 mm; Millipore, Bedford, Mass., USA).

The inner wall of the tubular adsorption device 1 was coated with an impregnated glass fibre filter (2.5×6 cm), and in the filter holder an impregnated 13 mm (inner diameter) round glass fibre filter was placed (filter device 2). The glass fibre filters were of type MG 160 with a pore size of 0.3 µm (Munktell, Grycksbo, Sweden). The filters were impregnated with reagent solutions containing equimolar amounts of DBA and acetic acid in methanol. The impregnation was performed by adding 1 ml of a 1.5 M DBA reagent solution to the adsorption device 1 and 0.1 ml of 0.7 M DBA reagent solution to the filter device 2. Before placing the filters inside the sampling device, the solvent was allowed to evaporate at room temperature for 1 h. A flow of 0.2 l min$^{-1}$ was achieved with air sampling pumps (Provtagaren AB, Hässleholm, Sweden) and a Dry-Cal® DCLite flow meter (BIOS International Corp., NJ, USA) was used to calibrate the sampling flows. After sampling, the sampling device was extracted with 3 ml of 1 mM $H_2SO_4$ (aq), 3 ml of methanol and 6 ml of toluene in a four step extraction procedure. All the extraction solutions were transferred to the same test tube.

The sampling device in combination with the DBA reagent collected a wide range of isocyanates in both gas and particle phase efficiently and with good repeatability. The sampler collected monoisocyanates predominately by diffusion towards the tube walls coated with impregnated glass-fibre filter, whereas the di- and polyisocyanates were mainly collected on the reagent-impregnated filter device 2. Isocyanate-DBA derivatives obtained were efficiently extracted from impregnated filters in the sampling device. The design of the sampling device enabled continuous refreshing of the reagent on the filter device 2 where particle-borne isocyanates were collected. As the reagent loading was in large excess and the volatility of DBA was reduced by using the reagent in combination with acetic acid, large volumes of air (8 h sampling) could be drawn through the solvent-free sampling device without changing its performance. This demonstrates the potential to use the sampling device for long-term sampling. After completed sampling, the formed isocyanate-DBA derivatives were found stable in the sampling device and, hence, field extractions were not necessary. In comparison with an impinger-filter reference method, the results obtained with the solvent-free sampling device were similar as to concentration and variation when evaluated in test chamber studies (RH 45 g) and in two field applications (with the exception of 3-ring MDI). Consequently, the solvent-free sampling device has many advantages when performing personal or area sampling and is a convenient alternative in most applications to the more cumbersome impinger filter sampler.

For analysis of isocyanate-DBA derivatives, a Quattro Micro tandem mass spectrometer (Waters, Altrincham, Cheshire, UK) was used in the electrospray mode monitoring positive ions (ESI+). The capillary voltage was 4.0 kV, the temperature of the ion source was 130° C. and the desolvation temperature was 200° C. Argon was used as collision gas, and the pressure of the collision cell was 4*10−3 mbar. Multiple reaction monitoring (MRM) was performed by monitoring 24 ions with a dwell time of 0.05 s and an interscan delay of 0.1 s. Quantitative measurements were made by MRM of $[M+H]^+ \rightarrow [130]^+$ of the isocyanate-DBA derivatives and $[M+H]^+ \rightarrow [139]^+$ of the isocyanate-$d_9$-DBA derivatives. The cone voltages and the collision energies were the same for MRM of DBA and $d_9$-DBA derivatives. The mass spectrometer was connected to a Shimadzu LC10ADVP micro-LC pump (Shimadzu Corporation, Kyoto, Japan). Loop injections of a centred sample plug of 2.5 µl in a 20 µl loop surrounded by 17.5 µl of focusing liquid (5/95 acetonitrile/water v/v) were made with a LC-PAL autosampler (CTC Analytics AG, Zwingen, Switzerland). Gradient elution was performed for the DBA-isocyanate derivatives using mobile phase A: 5/95/0.05 and B: 95/5/0.05 acetonitrile/water/formic acid (v/v/v) from 40% B to 100% B in 12 min with a flow rate of 70 µl min−1. The LC column was an Xterra® C18, 50 mm×1.0 mm with 2,5 µm particles (Waters, Mass., USA).

In a study of quantification of isocyanate-DBA derivatives, the isocyanate-DBA derivatives were determined using LC-MS/MS. Within the 12 minutes of gradient elution, all isocyanate-DBA derivatives in the study were resolved on the LC column. No interfering peaks from the reagent or from "blanks" for both the solvent-free sampling device and the impinger-filter sampler were observed in the MS/MS chromatograms. Quantifications of the isocyanate-DBA derivatives were made by performing MRM and peak area ratio measurements of $[M+H]^+ \rightarrow [130]^+$ for the isocyanate-DBA and of $[M+H]^+ \rightarrow [139]^+$ for the isocyanate-$d_9$-DBA derivatives (internal standards). For quantification of air samples collected in the test chamber or in the field measurements, calibration curves for the solvent free samples were in the range 0-0.28 µg ml$^{-1}$, and for the impinger-filter samples 0-1.4 µg ml$^{-1}$. The calibration graphs were linear in the range investigated, with correlation coefficients>0.995 for all isocyanate-DBA derivatives.

The instrumental precision for 10 repeated injections of a sample containing isocyanate-DBA derivatives at 0.1 µg ml$^{-1}$ was <2%. The instrumental detection limits for the isocyanate-DBA derivatives were in the range 0.01-5 fmol. DBA and DBA derivatives in the solvent-free sampling device extraction of isocyanate-DBA derivatives from the sampler. The extraction of isocyanate-DBA derivatives from the sampling device was performed using the 4 step extraction procedure with 3 different extraction media. Within the experimental errors, no significant losses were observed, and the total yield was within 91-106%. Initial attempts to extract the DBA derivatives from the sampling device showed that both hydrophilic and hydrophobic extraction was necessary. In the first extraction, an aqueous phase was used in order to efficiently wet the filter and to dissolve the DBA acetic acid salt. The following extraction with methanol made the filter more hydrophobic, and in this step the major part of the derivatives was extracted. In the last two steps with toluene, the last parts of the hydrophobic isocyanate-DBA derivatives were extracted.

The invention claimed is:
1. A sampling device for analysis of a substance, wherein the substance is selected from the group consisting of isocyanates, aminoisocyanates, isothiocyanates, anhydrides, amines and carboxylic acids and can be present in both gas and particle phases in an air flow passed, for sampling, through the sampling device, said sampling device comprising:

a) an adsorption device comprising a coating, wherein said coating comprises a mixture of one or more primary or secondary amines as reagent and an acidic compound having the ability to form a salt with the amine(s), wherein the reagent is for adsorption of and reaction with the substance in the gas phase of the air flow and the acidic compound is for immobilization of the reagent in said adsorption device; and b) a filter device comprising said mixture of reagent amine(s) and acidic compound for adsorption of and reaction with the substance in the particle phase of the air flow.

2. The sampling device according to claim 1, wherein the adsorption device is tubular in the air flow direction, and wherein the ratio of the length to the inner diameter of the adsorption device is greater than 5, and preferably about 10.

3. The sampling device according to claim 2, wherein the inner walls of the adsorption device are coated with the mixture of reagent and acidic compound and/or wherein a strip inserted in the adsorption device is coated with the mixture.

4. The sampling device according to claim 1, wherein the adsorption device is tubular in the air flow direction, and wherein the ratio of the length to the inner diameter of the adsorption device is about 10.

5. The sampling device according to claim 1, wherein the acidic compound comprises a carboxylic acid.

6. The sampling device according to claim 5, wherein the mixture contains one or more different carboxylic acids.

7. The sampling device according to claim 6, wherein the mixture contains one or more different carboxylic acids selected from the group consisting of formic acid, acetic acid and propionic acid.

8. The sampling device according to claim 1, wherein the reagent is di-n-butylamine.

9. The sampling device according to claim 1, wherein the primary or secondary amines are volatile in unbound form and each has a molecular weight less than 300.

10. The sampling device according to claim 1, wherein the adsorption device has an upper end and a lower end, wherein the lower end of the adsorption device is connected to an upper end of the filter device and wherein the filter device, further, has a lower end.

11. The sampling device according to claim 10, wherein an air inlet is arranged in the upper end of the adsorption device and wherein an air outlet is arranged in the lower end of the filter device.

12. The sampling device according to claim 10, wherein the sampling device is inverted in such manner that the air inlet is arranged in the lower end of the filter device and that the air outlet is arranged in the upper end of the adsorption device.

13. A sampling device according to claim 1, further comprising a pump or suction device to provide the passage of the air flow through the adsorption device and the filter device, wherein said pump or suction device is connected either to the adsorption device or to the filter device.

14. The sampling device according to claim 13, wherein the pump or suction device is connected to the lower end of the filter device.

15. The sampling device according to claim 14, wherein the pump or suction device is a vacuum tube or a displacement pump.

16. The sampling device according to claim 15, wherein the pump or suction device is selected from the group consisting of a hose pump, a diaphragm pump, an injection pump and a gear-type pump.

17. The sampling device according to claim 1, wherein the adsorption device consists of a body packed with particles that are coated with the mixture of reagent and acidic compound.

18. The sampling device according to claim 1, wherein the filter device is formed as a substantially flat cylinder having a diameter greater than or equal to that of the adsorption device, wherein the filter device contains particles that are coated with the reagent and mixed with the acidic compound, and wherein the filter device has an average pore diameter of 0.1-20 µm, preferably 0.2-2 µm, and most preferably 0.4 µm.

19. The sampling device according to claim 1, comprising a reagent container containing the reagent, the reagent container being connected to the adsorption device and/or the filter device by means of a switch device for conveying the reagent to the adsorption device and/or the filter device for reaction therein with the non-reacted substance.

20. The sampling device according to claim 19, wherein the reagent container is connected by means of the switch device to the adsorption device or the filter device for automatic conveyance thereto of reagent after completed sampling and closing of the air inlet and the air outlet, respectively, for reaction with residual non-reacted substance in the sampling device.

21. The sampling device according to claim 20, wherein the reagent container is arranged as a concentric tube around the adsorption device.

22. The sampling device according to claim 1, wherein the adsorption device and the filter device are enclosed in a uniform casing having a closable air inlet and outlet, respectively.

23. A kit comprising a plurality of sampling devices according to claim 1 for taking samples from a plurality of the different substances at the same time or at different points of time, the reagent in each sampling device being selected for the substance with which it is to react in the air flow.

24. A method for taking samples from a substance by means of a sampling device according to claim 14, wherein the substance is selected from the group consisting of isocyanates, aminoisocyanates, isothiocyanates, anhydrides, amines and carboxylic acids and can be present in both gas and particle phase in an air flow, the method comprising the steps of:

passing an air flow through the adsorption device and the filter device of the sampling device via an air inlet and air outlet;

closing the air inlet and the air outlet of the sampling device after the passage of a predetermined volume of air, the switch device associated with the reagent container automatically securing conveyance of the reagent therein to the adsorption device and the filter device for reaction therein with the residual, non-reacted substance; and subjecting any said substance captured in the sampling device to a qualitative and/or quantitative analysis.

25. The method according to claim 24, characterized in that it further comprises carrying out an initial activation step, in which a mixture of the reagent and the carboxylic acid is added to the adsorption device and the filter device immediately before the initiation of the sampling.

26. The method according to claim 24, characterized in that isocyanates, anhydrides, aminoisocyanates, isothiocyantes, amines and carboxylic acids are adsorbed by and react with di-n-butylamine in the sampling device.

27. The method according to claim 24, characterized in that an air flow of 0.001-1 l/min, and preferably 10-100 ml/min, is passed through the sampling device.

28. A method for immobilization of volatile primary and secondary amines, preferably di-n-butylamine, on a surface, characterized in that:

the volatile primary or secondary amine is mixed with a carboxylic acid, preferably formic acid, acetic acid or propionic acid, and that the surface is subsequently coated with the prepared mixture;

one or more different primary and/or secondary amines, preferably di-n-butylamine, is/are immobilized in an adsorption device and/or a filter device in a sampling device or a kit according to claim 1.

29. A method for immobilization of volatile primary and secondary amines, preferably di-n-butylamine, on a surface, characterized in that the volatile primary or secondary amine is mixed with a carboxylic acid, preferably formic acid, acetic acid or propionic acid, and that the surface is subsequently coated with the prepared mixture.

* * * * *

UNITED STATES PATENT AND TRADEMARK OFFICE
CERTIFICATE OF CORRECTION

PATENT NO. : 7,700,045 B2
APPLICATION NO. : 11/361689
DATED : April 20, 2010
INVENTOR(S) : :Skarping et al.

Page 1 of 1

It is certified that error appears in the above-identified patent and that said Letters Patent is hereby corrected as shown below:

Column 9, line 58, "(RH 45g)" should read -- (RH 45%) --.

Signed and Sealed this
Twenty-eighth Day of December, 2010

David J. Kappos
*Director of the United States Patent and Trademark Office*